(12) United States Patent
Kim et al.

(10) Patent No.: US 8,603,114 B2
(45) Date of Patent: Dec. 10, 2013

(54) ANASTOMOTIC DEVICE FOR TUBULAR ORGAN

(75) Inventors: Cheol Woong Kim, Seoul (KR); Ho Sang Lee, Seoul (KR)

(73) Assignee: Triple-C Medical Corporation, Seoul (KR)

( * ) Notice: Subject to any disclaimer, the term of this patent is extended or adjusted under 35 U.S.C. 154(b) by 121 days.

(21) Appl. No.: 13/120,367

(22) PCT Filed: Aug. 3, 2009

(86) PCT No.: PCT/KR2009/004334
§ 371 (c)(1),
(2), (4) Date: Apr. 26, 2011

(87) PCT Pub. No.: WO2010/035953
PCT Pub. Date: Apr. 1, 2010

(65) Prior Publication Data
US 2011/0251628 A1 Oct. 13, 2011

(30) Foreign Application Priority Data

Sep. 23, 2008 (KR) .................... 10-2008-0093211
Sep. 25, 2008 (KR) .................... 10-2008-0094056

(51) Int. Cl.
*A61B 17/11* (2006.01)
*A61B 17/115* (2006.01)

(52) U.S. Cl.
USPC ............ 606/150; 606/139; 606/148; 606/153

(58) Field of Classification Search
USPC ............ 606/1, 139, 144, 148, 150, 153, 205, 606/215–218; 285/38–39; 81/90.2, 128, 81/155
See application file for complete search history.

(56) References Cited

U.S. PATENT DOCUMENTS 2,549,731 A * 4/1951 Wattley ................... 439/482
3,154,281 A * 10/1964 Frank ..................... 248/201

(Continued)

FOREIGN PATENT DOCUMENTS

EP 1842495 10/2007
JP 2005-095564 4/2005

OTHER PUBLICATIONS

International Search Report mailed Feb. 24, 2010, for PCT/KR2009/004334.
English language abstract of JP 2005-095564.

*Primary Examiner* — Corrine M McDermott
*Assistant Examiner* — Mark Mashack
(74) *Attorney, Agent, or Firm* — Rabin & Berdo, P.C.

(57) ABSTRACT

Provided is an anastomotic device including a first holder and a second holder for holding a first anastomotic ring and a second anastomotic ring, respectively, a first slave body which is connected to the first holder, and which has a first slave surface, a second slave body which is connected to the second holder, and which has a second slave surface, a first driving body which has a first driving surface sliding along the first slave surface, and which moves along a predetermined direction, and a second driving body which has a second driving surface sliding along the second slave surface, and which moves along the predetermined direction. The first slave body moves toward the second slave body and the second slave body moves toward the first slave body by the movements of the first driving body and the second driving body.

15 Claims, 11 Drawing Sheets

(56) References Cited

U.S. PATENT DOCUMENTS

| | | | |
|---|---|---|---|
| 3,316,914 A * | 5/1967 | Collito | 606/150 |
| 3,561,448 A * | 2/1971 | Peternel | 606/148 |
| 4,245,638 A * | 1/1981 | Lebeck et al. | 606/150 |
| 4,316,470 A * | 2/1982 | Braun et al. | 606/150 |
| 4,607,637 A * | 8/1986 | Berggren et al. | 606/153 |
| 4,624,257 A | 11/1986 | Berggren | |
| 4,872,709 A * | 10/1989 | Stack | 285/39 |
| 4,917,090 A * | 4/1990 | Berggren et al. | 606/153 |
| 4,917,091 A * | 4/1990 | Berggren et al. | 606/153 |
| 5,582,617 A * | 12/1996 | Klieman et al. | 606/170 |
| 5,707,379 A * | 1/1998 | Fleenor et al. | 606/145 |
| 5,722,990 A * | 3/1998 | Sugarbaker et al. | 606/207 |
| 5,788,689 A * | 8/1998 | Allan et al. | 606/1 |
| 5,954,731 A * | 9/1999 | Yoon | 606/144 |
| 6,074,408 A * | 6/2000 | Freeman | 606/205 |
| 7,918,866 B2 * | 4/2011 | Geitz | 606/142 |
| 2004/0097988 A1 * | 5/2004 | Gittings et al. | 606/153 |
| 2004/0215221 A1 * | 10/2004 | Suyker et al. | 606/153 |
| 2005/0101976 A1 | 5/2005 | Kato | |
| 2005/0215993 A1 * | 9/2005 | Phan | 606/41 |
| 2005/0277959 A1 * | 12/2005 | Cosgrove et al. | 606/151 |
| 2006/0264981 A1 * | 11/2006 | Viola | 606/153 |
| 2007/0239180 A1 | 10/2007 | Kuester, III | |
| 2008/0154288 A1 * | 6/2008 | Belson | 606/150 |
| 2012/0165844 A1 * | 6/2012 | Roth et al. | 606/153 |

\* cited by examiner (a)

(b)

(c)

(a)

(b)

(c)

ANASTOMOTIC DEVICE FOR TUBULAR ORGAN

TECHNICAL FIELD

The present invention disclosed herein relates to a device configured to perform an anastomosis on a tubular organ such as a blood vessel, and more particularly, to an anastomotic device including anastomotic rings.

BACKGROUND ART

A free flap is used to reconstruct various parts of the body with absent soft tissues, or for functional and aesthetic purposes. Following the first successful implementation of the free flap in 1973 by Daniel and Taylor, it has been significantly developed. The free flap is mainly used in vascular anastomoses. However, vascular anastomoses using minute sutures require much time in mastering the suture technique as well as long operation time. Moreover it carries the risk for thrombosis and total flap failure. To address these limitations, a vascular anastomosis using a minute coupling ring was developed in 1962 by Komei Nakayama et al. Since Komei Nakayama et al first introduced a vascular anastomosis using an anastomotic ring for reconstructing an oesophagus, many experimental and clinical works on mechanical anastomoses have been developed.

The mechanical anastomoses have the following characteristics. First, the mechanical anastomosis is more accurate and requires less time in mastering the operation technique than a vascular anastomosis using a suture. Secondly, it takes just about 2 to 3 minutes to perform the mechanical anastomosis. Thirdly, a monitoring result after the mechanical anastomosis is not worse than the vascular anastomosis using a suture. Fourthly, even when the diameter of a donor vessel is significantly different from that of a recipient vessel, the difference thereof can be efficiently reduced. Fifthly, the mechanical anastomosis can be efficiently performed even in a limited (small) space and a deep area of a body.

DISCLOSURE

Technical Problem

The present invention provides an anastomotic device that makes it possible to efficiently and quickly perform an anastomosis on a tubular organ such as a blood vessel.

The details of one or more embodiments are set forth in the accompanying drawings and the description below.

Technical Solution

Embodiments of the present invention provide anastomotic devices including: a first holder and a second holder for holding a first anastomotic ring and a second anastomotic ring, respectively; a first slave body which is connected to the first holder, and which has a first slave surface; a second slave body which is connected to the second holder, and which has a second slave surface; a first driving body which has a first driving surface sliding along the first slave surface, and which moves along a predetermined direction; and a second driving body which has a second driving surface sliding along the second slave surface, and which moves along the predetermined direction, wherein the first slave body moves toward the second slave body and the second slave body moves toward the first slave body by the movements of the first driving body and the second driving body.

In some embodiments, the first slave surface may include a first slave inclination surface that is inclined outward to a front side of the first driving body, and a first slave plane that extends approximately in the predetermined direction from a front end of the first slave inclination surface, and the first driving surface may include a first driving inclination surface that is inclined outward to the front side of the first driving body, and a first driving plane that extends approximately in the predetermined direction from a rear end of the first driving inclination surface, wherein, when the first driving inclination surface slides along the first slave inclination surface, the first salve body moves toward the second slave body.

In other embodiments, when the first driving plane slides along the first slave plane, the first slave body may be in a stop state.

In still other embodiments, the anastomotic devices may further include: a separation bar moving toward the first and second holders along the predetermined direction in the stop state to separate the first and second anastomotic rings from the first and second holders; and a front case having a front end to which the separation bar and the first and second driving bodies are fixed, wherein, when the front case moves along the predetermined direction, the separation bar and the first and second driving bodies move along the predetermined direction.

In even other embodiments, the anastomotic devices may further include: a separation bar moving toward the first and second holders along the predetermined direction to separate the first and second anastomotic rings from the first and second holders; and a front case having a front end to which the separation bar and the first and second driving bodies are fixed, wherein, when the front case moves along the predetermined direction, the separation bar and the first and second driving bodies move along the predetermined direction.

In yet other embodiments, the anastomotic devices may further include: a middle case having a first thread on an inner circumferential surface thereof; and a screw shaft which has a second thread on an outer circumferential surface thereof to correspond to the first thread, and which has a front end connected to the front case to move along the predetermined direction by a rotation of the screw shaft.

In further embodiments, the anastomotic devices may further include: a rear case disposed behind the front case; a pinion disposed inside the rear case; a rotation lever connected to the pinion to rotate the pinion; and a rack member which has a front end holding the front case to move together with the front case, and which includes a rack engaging with the pinion and moving along the predetermined direction by a rotation of the pinion.

In still further embodiments, the anastomotic devices may further include a first rotator that includes a first guide recess connected to the first holder and extending in a direction approximately perpendicular to the predetermined direction, wherein the first holder includes a first protrusion that is inserted in the first guide recess and moves along the first guide recess.

In even further embodiments, the anastomotic devices may further include: a first rotator connected to the first holder; a driving shaft including a driving gear and having a front end to which the first rotator is fixed; a second rotator connected to the second holder; and a slave shaft which includes a driven gear engaging with the driving gear to rotate, and which has a front end to which the second rotator is fixed; wherein the first holder rotates toward the second holder and the second holder rotates toward the first holder by a rotation of the driving shaft.

In yet further embodiments, the anastomotic devices may further include: a first rotator connected to the first holder; a first driving shaft including a first driving gear and a first driven gear and having a front end to which the first rotator is fixed; a second rotator connected to the second holder; a slave shaft which includes a second driven gear engaging with the first driving gear to rotate, and which has a front end to which the second rotator is fixed; and a second driving shaft including a second driving gear engaging with the first driven gear to rotate, wherein the first holder rotates toward the second holder and the second holder rotates toward the first holder by the rotation of the second driving shaft.

In much further embodiments, the first driven gear may include a ring gear, and the second driving gear may include a pinion engaging with an inner part of the ring gear. In addition, the second driving shaft may be disposed between the first driving shaft and the slave shaft.

In still much further embodiments, the anastomotic devices may further include a first rotator that includes a first front guide recess and a first rear guide recess, wherein the first front guide recess is connected to the first holder and extends in a direction approximately perpendicular to the predetermined direction, the first rear guide recess is connected to the first slave body and extends in the direction approximately perpendicular to the predetermined direction, the first holder includes a first front protrusion that is inserted in the first front guide recess to move along the first front guide recess, and the first slave body includes a first rear protrusion that is inserted in the first rear guide recess to move along the first rear guide recess.

In yet much further embodiments, the anastomotic devices may further include: a first front elastic body inserted in the first front guide recess to apply elastic force to the first holder such that first holder returns from the second holder; and a first rear elastic body inserted in the first rear guide recess to apply elastic force to the first slave body such that first slave body returns from the second slave body.

Advantageous Effects

According to the embodiments of the present invention, an anastomosis can be efficiently and quickly performed on a tubular organ such as a blood vessel.

DESCRIPTION OF DRAWINGS

The accompanying drawings are included to provide a further understanding of the present invention, and are incorporated in and constitute a part of this specification. The drawings illustrate exemplary embodiments of the present invention and, together with the description, serve to explain principles of the present invention. In the drawings.

BEST MODE

Figure 1:
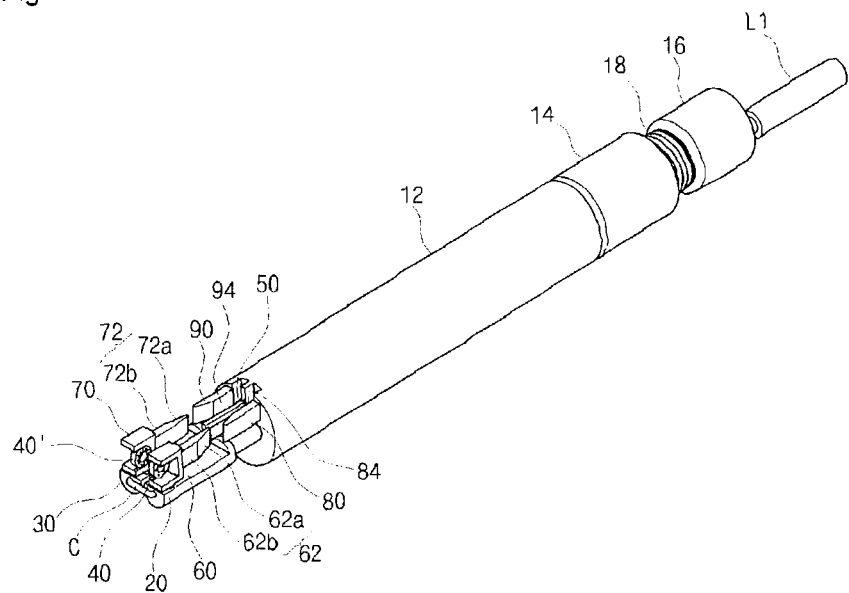
FIG. 1 is a perspective view illustrating an anastomotic device according to an embodiment of the present invention.

Preferred embodiments of the present invention will be described below in more detail with reference to FIGS. 1 through 15. The present invention may, however, be embodied in different forms and should not be constructed as limited to the embodiments set forth herein. Rather, these embodiments are provided so that this disclosure will be thorough and complete, and will fully convey the scope of the present invention to those skilled in the art. In the drawings, the dimensions of elements may be exaggerated for clarity of illustration.

While blood vessels are exemplified in the following embodiments, it will be understood by those skilled in the art that various changes in form and details may be made therein without departing from the spirit and scope of the present invention. In addition, the present invention may be applied to various types of minute surgeries such as a reconstruction using a free flap method, an anastomosis of a cut blood vessel, an intestinal anastomosis, a treatment of a heart disease, and other anastomoses of tubular organs.

Figure 2:
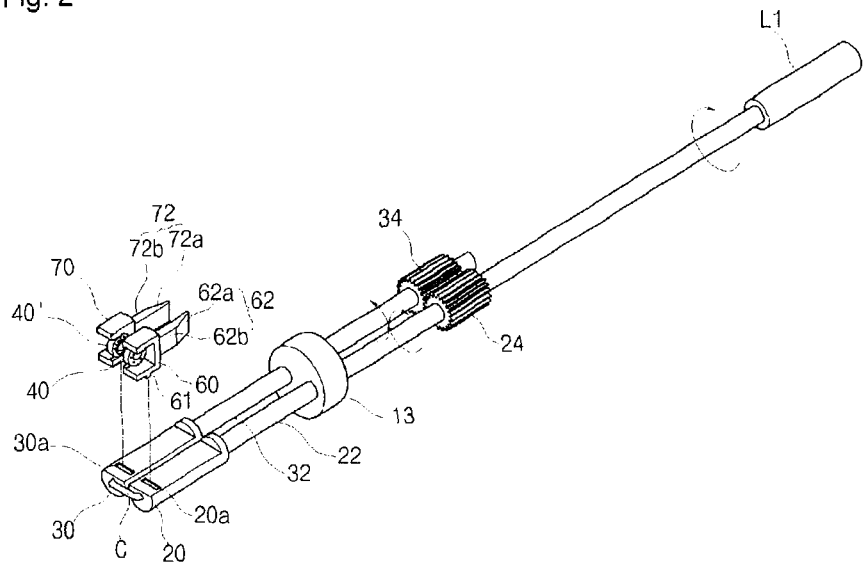
FIG. 2 is a perspective view illustrating the anastomotic device of FIG. 1, without a front case, a middle case, and a rear case.

FIG. 1 is a perspective view illustrating an anastomotic device according to an embodiment of the present invention. FIG. 2 is a perspective view illustrating the anastomotic device of FIG. 1, without a front case, a middle case, and a rear case. Referring to FIGS. 1 and 2, the anastomotic device includes a first holder 60 and a second holder 70. The first and second holders 60 and 70 have an approximately U shape, and are connected to a first rotator 20 and a second rotator 30, respectively, to fix anastomotic rings 40 and 40' during a medical treatment. After the medical treatment, the anastomotic rings 40 and 40' are removed from the first and second holders 60 and 70. A first slave body 62 and a second slave body 72 are disposed at the rear ends of the first and second holders 60 and 70, respectively. The first and second slave bodies 62 and 72 move according to movements of a first driving body 80 and a second driving body 90, and a moving direction of the first and second driving bodies 80 and 90 is approximately perpendicular to that of the first and second slave bodies 62 and 72, which will be described later.

Referring to FIG. 2, the first slave body 62 has a first slave surface contacting the first driving body 80 to be described later. The first slave surface includes a first slave inclination surface 62a and a first slave plane 62b. The first slave inclination surface 62a is inclined outward to the front side of the first driving body 80, and the first slave plane 62b extends approximately in the moving direction of the first driving body 80 from the front end of the first slave inclination surface 62a. In a same manner, the second slave body 72 has a second slave surface contacting the second driving body 90 to be described later. The second slave surface includes a second slave inclination surface 72a and a second slave plane 72b. The second slave inclination surface 72a is inclined outward to the front side of the second driving body 90, and the second slave plane 72b extends approximately in the moving direction of the second driving body 90 from the front end of the second slave inclination surface 72a. The first and second slave surfaces will be described later in detail.

As illustrated in FIG. 2, the first and second rotators 20 and 30 are disposed at the front end of a driving shaft 22 and the front end of a slave shaft 32, respectively. The driving shaft 22 and the first rotator 20 rotate together. The slave shaft 32 and the second rotator 30 rotate together. A clip C includes pins that are inserted in rotation centers of the first and second rotators 20 and 30, respectively. The pins prevent the movement of the first and second rotators 20 and 30 while the first and second rotators 20 and 30 rotate. The first and second rotators 20 and 30 rotate about the pins inserted in the rotation centers thereof.

The first and second rotators 20 and 30 include a first guide recess 20a and a second guide recess 30a, respectively. The first and second guide recesses 20a and 30a extend approximately in the moving direction of the first and second slave bodies 62 and 72. The first holder 60 includes a first protrusion 61, which is inserted in the first guide recess 20a and moves along the first guide recess 20a. According to a movement of the first slave body 62, the protrusion 61 moves together with the first holder 60 along the first guide recess 20a. In a same manner, the second holder 70 includes a second protrusion (not shown) that moves along the second guide recess 30a. That is, according to a movement of the second slave body 72, the second protrusion moves together with the second holder 70 along the second guide recess 30a. Accordingly, the anastomotic rings 40 and 40' fixed to the first and second holders 60 and 70 are coupled to each other, which will be described later.

The driving shaft 22 and the slave shaft 32 pass through a fixing member 13. A driving gear 24 is installed on the driving shaft 22. A driven gear 34 is installed on the slave shaft 32. The driving gear 24 rotates together with the driving shaft 22, and the driven gear 34 rotates together with the slave shaft 32. The driven gear 34 engages with the driving gear 24 and rotates according to a rotation of the driving gear 24. A driving lever L1 is disposed at the rear end of the driving shaft 22. The driving shaft 22 and the slave shaft 32 will be described later in detail.

Referring to FIG. 1, the anastomotic device includes a front case 12, a middle case 14, a rear case 16, and a screw shaft 18. The first and second driving bodies 80 and 90 and a separation bar 50 are fixed to the front end of the front case 12, and the middle case 14 is disposed between the front case 12 and the rear case 16. The driving shaft 22 and the slave shaft 32 are exposed out of the front case 12 through the front end of the front case 12. The first and second holders 60 and 70, and the first and second rotators 20 and 30 are disposed at the front side of the front case 12. The driving lever L1 is exposed out of the rear case 16 through the rear end of the rear case 16. The front case 12, the middle case 14, and the rear case 16 may have an approximately circular or polygonal cylinder shape.

FIGS. 3 through 6 are schematic views illustrating rotations of the first and second holders according to rotations of the driving shaft and the slave shaft, illustrated in FIG. 2. In the state where the driving gear 24 engages with the driven gear 34 as illustrated in FIG. 2, when the driving lever L1 connected to the rear end of the driving shaft 22 is rotated clockwise, the driving gear 24 rotates to rotate the driven gear 34 counterclockwise, and thus, the slave shaft 32 rotates counterclockwise.

Figure 3:
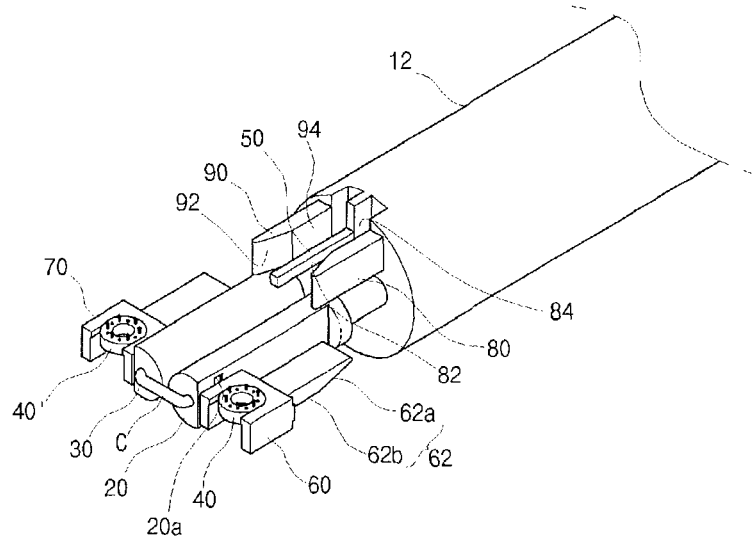
FIGS. 3 through 6 are schematic views illustrating rotations of first and second holders according to rotations of a driving shaft and a slave shaft, illustrated in FIG. 2.
Figure 4:
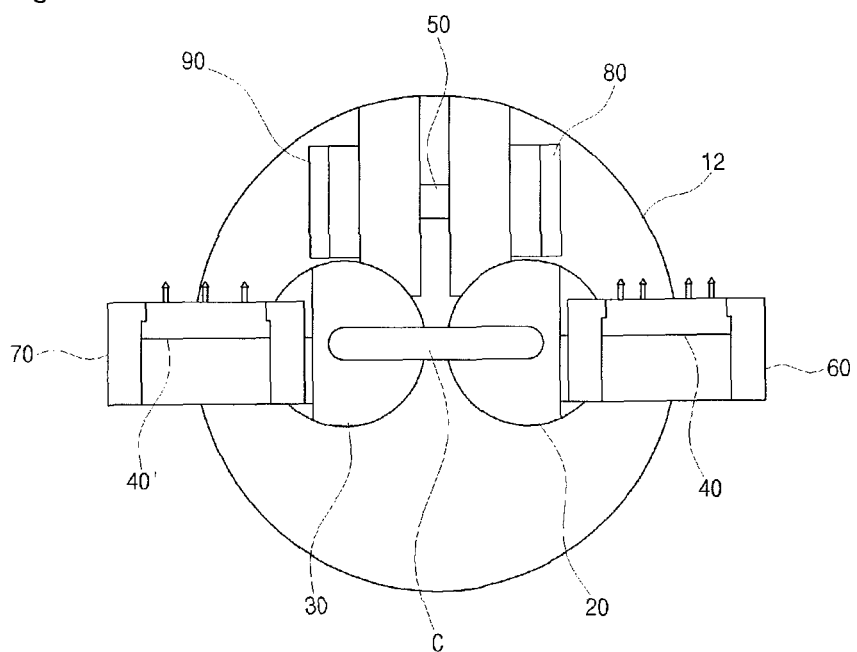
Figure 5:
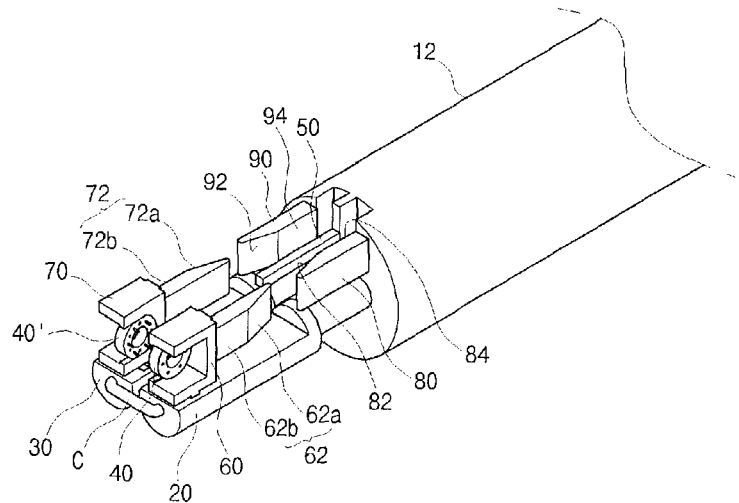
Figure 6:
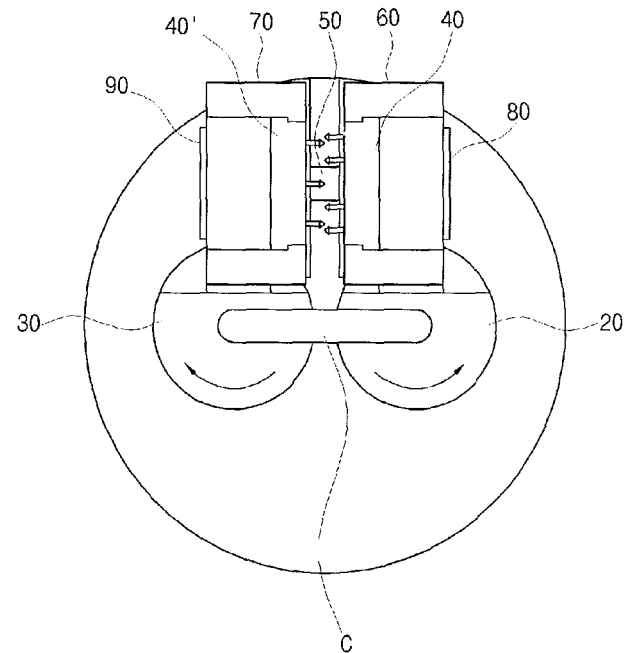

In the state where the anastomotic rings 40 and 40' fixed respectively to the first and second holders 60 and 70 are disposed on approximately the same plane as illustrated in FIGS. 3 and 4, when the driving lever L1 is rotated, the first and second holders 60 and 70 rotate. According to the rotation of the first rotator 20, the anastomotic ring 40 fixed to the first holder 60 is rotated counterclockwise to the second holder 70. According to the rotation of the second rotator 30, the anastomotic ring 40' fixed to the second holder 70 is rotated clockwise to the first holder 60. Referring to FIGS. 5 and 6, according to the rotations of the first and second holders 60 and 70, the anastomotic rings 40 and 40' fixed to the first and second holders 60 and 70 face each other.

Figure 7:
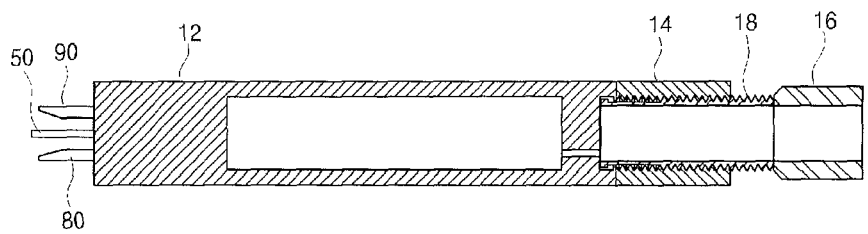
FIGS. 7 and 8 are cross-sectional views illustrating a movement of the front case according to a rotation of the rear case of FIG. 1.
Figure 8:
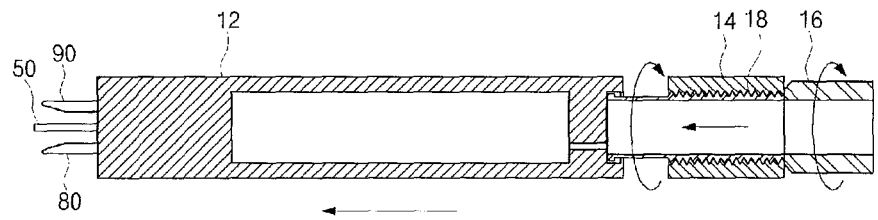
Figure 9:
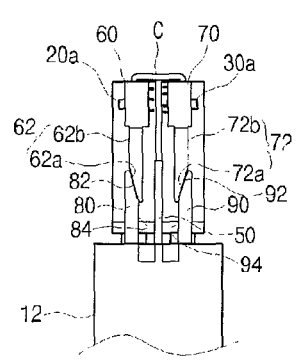
FIGS. 9A, 9B and 9C are schematic views sequentially illustrating movements of first and second slave bodies according to movements of the front case and first and second driving bodies of FIG. 1.
Figure 9:
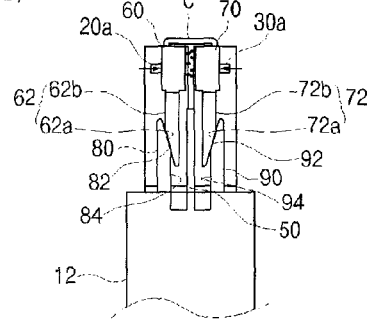
Figure 9:
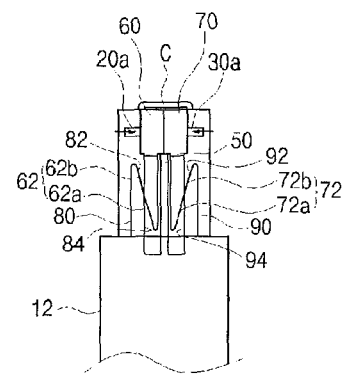

FIGS. 7 and 8 are cross-sectional views illustrating a movement of the front case according to a rotation of the rear case of FIG. 1. Referring to FIG. 7, the front end of the screw shaft 18 is connected to the rear end of the front case 12. The screw shaft 18 freely rotates at the rear end of the front case 12, and torque of the screw shaft 18 is not transmitted to the front case 12. However, when the screw shaft 18 moves forward or rearward, the front case 12 connected to the screw shaft 18 is moved forward or rearward together with the screw shaft 18, which will be described later. The rear end of the screw shaft 18 is connected to the front end of the rear case 16. When the rear case 16 rotates, the screw shaft 18 rotates together with the rear case 16.

The screw shaft 18 passes through the middle case 14. An outer circumferential surface of the screw shaft 18 is provided with a thread. An inner circumferential surface of the middle case 14 is also provided with a thread. The thread of the middle case 14 engages with the thread of the screw shaft 18.

Referring to FIG. 8, when the rear case 16 rotates in a predetermined direction, the thread of the screw shaft 18 moves along the thread of the middle case 14, and the screw shaft 18 moves forward. According to the forward movement of the screw shaft 18, the front case 12 also moves forward. On the contrary, when the screw shaft 18 rotates in the opposite direction to the predetermined direction, the thread of the screw shaft 18 moves along the thread of the middle case 14, and the screw shaft 18 moves rearward. According to the rear movement of the screw shaft 18, the front case 12 also moves rearward.

Figure 10:
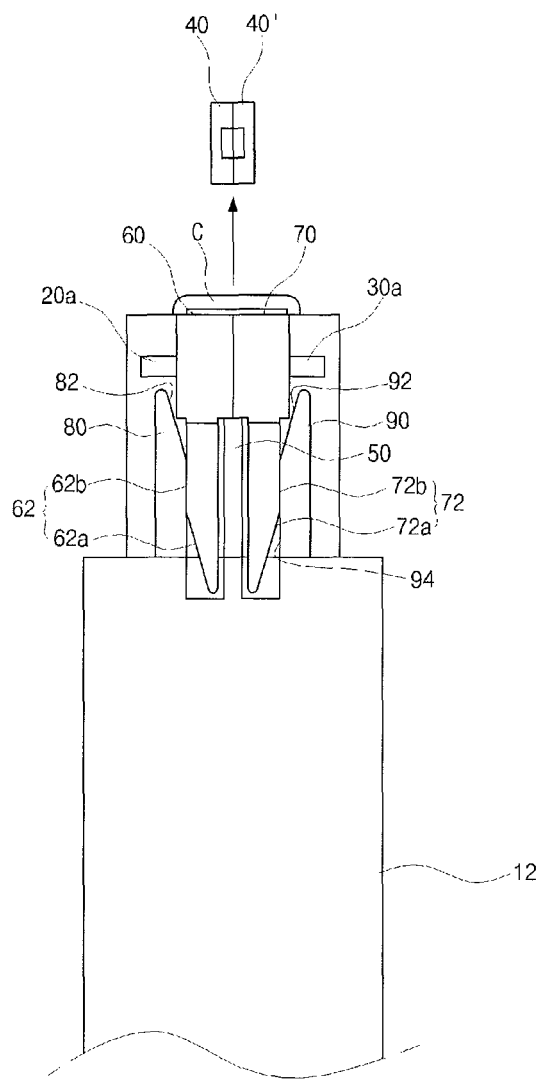
FIG. 10 is a schematic view illustrating a state where anastomotic rings are separated according to movements of the front case and a separation bar of FIG. 1.

FIGS. 9A, 9B and 9C are schematic views sequentially illustrating movements of the first and second slave bodies according to movements of the front case and the first and second driving bodies of FIG. 1. FIG. 10 is a schematic view illustrating a state where the anastomotic rings are separated according to movements of the front case and the separation bar of FIG. 1.

As described above, the separation bar 50 and the first and second driving bodies 80 and 90, fixed to the front end of the front case 12, move together with the front case 12. Referring to FIG. 9A, as the front case 12 moves forward, a first driving inclination surface 82 of the first driving body 80 contacts the first slave inclination surface 62a of the first slave body 62, and a second driving inclination surface 92 of the second driving body 90 contacts the second slave inclination surface 72a of the second slave body 72.

In this state, when the front case 12 moves forward, the first driving inclination surface 82 moves along the first slave inclination surface 62a to apply force to the first slave inclination surface 62a, and thus, the first slave body 62 moves to the second slave body 72. In a same manner, the second driving inclination surface 92 moves along the second slave inclination surface 72a to apply force to the second slave inclination surface 72a, and thus, the second slave body 72 moves to the first slave body 62. Accordingly, as illustrated in FIGS. 9B and 9C, the first and second slave bodies 62 and 72 come close to each other, and the first and second holders 60 and 70 also come close to each other, together with the first and second slave bodies 62 and 72. The moving direction of the first and second slave bodies 62 and 72 is approximately perpendicular to the forward moving direction of the front case 12.

The first protrusion 61 of the first holder 60 and the second protrusion of the second holder 70 move along the first and second guide recesses 20a and 30a, respectively. Accordingly, the anastomotic rings 40 and 40' come close to each other and are coupled to each other.

When the anastomotic rings 40 and 40' fixed to the first and second holders 60 and 70 are coupled to each other, the first and second driving inclination surfaces 82 and 92 are removed from the first and second slave inclination surfaces 62a and 72a, and the first and second driving inclination surfaces 82 and 92 do not apply force to the first and second slave inclination surfaces 62a and 72a any more. After that, as illustrated in FIG. 9C, as the front case 12 moves forward, a first driving plane 84 and a second driving plane 94 move along the first and second slave planes 62b and 72b.

After that, as illustrated in FIG. 10, the separation bar 50 moves forward together with the front case 12, and the separation bar 50 pass through a space disposed between the first and second holders 60 and 70 to push out the anastomotic rings 40 and 40' from the first and second holders 60 and 70. Thus, the anastomotic rings 40 and 40' are removed from the first and second holders 60 and 70.

Figure 11:
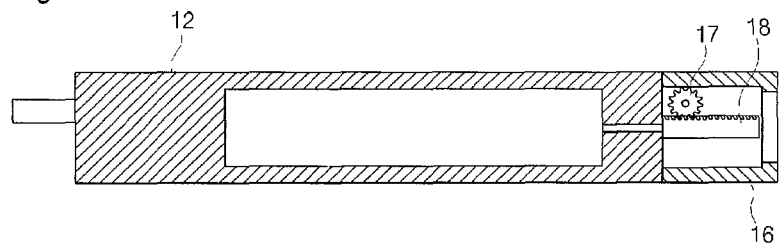
FIGS. 11 through 13 are schematic views illustrating movements of a front case and a rack member according to a rotation of a pinion according to an embodiment of the present invention.
Figure 12:
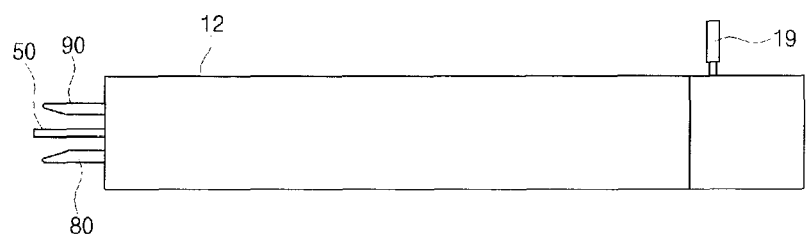
Figure 13:
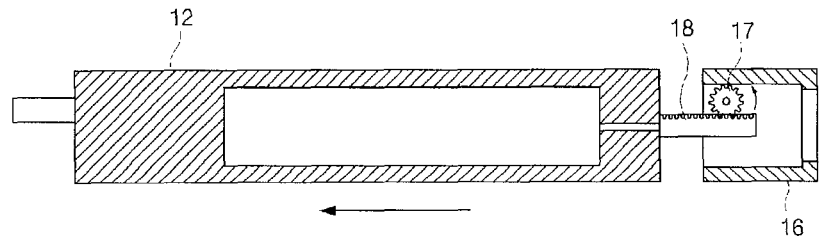

FIGS. 11 through 13 are schematic views illustrating movements of a front case and a rack member according to a rotation of a pinion according to an embodiment of the present invention. Unlike the above-described anastomotic device of FIGS. 7 and 8, a rack member 18 is disposed at the rear end of the front case 12 and includes a rack. A pinion 17 is disposed within the rear case 16 and engages with the rack of the rack member 18. The pinion 17 is connected to a rotation lever 19 disposed outside the rear case 16. When the rotation lever 19 rotates, the pinion 17 rotates together with the rotation lever 19.

Referring to FIG. 11, in the state where the rear end of the front case 12 contacts the front end of the rear case 16, when the rotation lever 19 is rotated, the pinion 17 is rotated together with the rotation lever 19. Referring to FIG. 13, as the pinion 17 rotates, the rack member 18 moves forward, and the front case 12 also moves forward together with the rack member 18.

Figure 14:
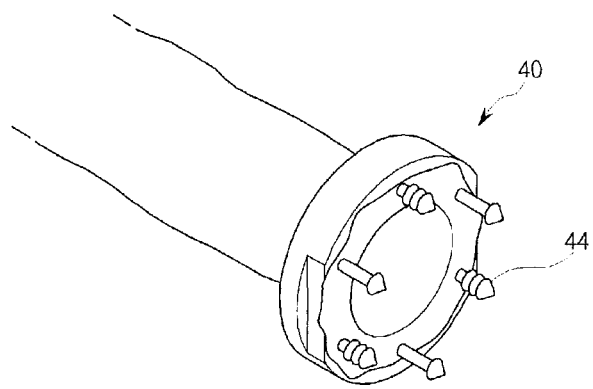
FIG. 14 is a perspective view illustrating a state where the anastomotic ring of FIG. 1 is installed on a blood vessel.
Figure 15:
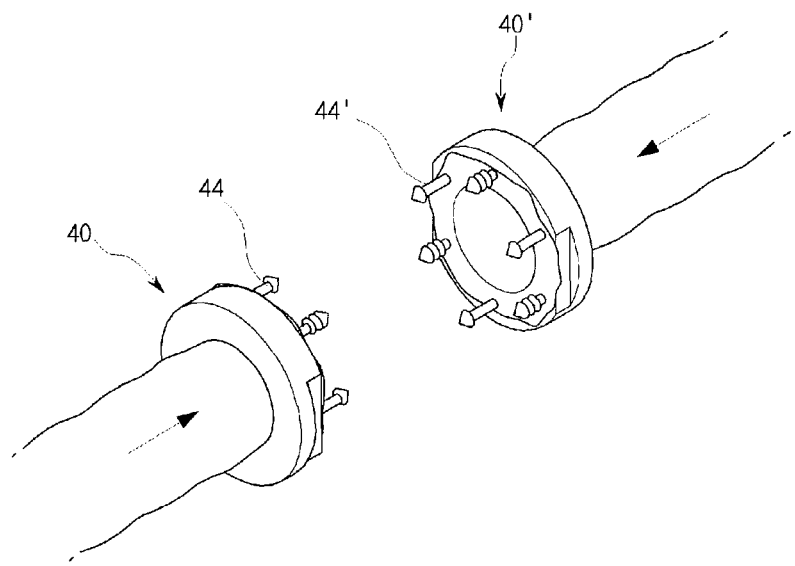
FIG. 15 is a perspective view illustrating an anastomosis method using the anastomotic rings of FIG. 1.

FIG. 14 is a perspective view illustrating the anastomotic ring 40 installed on a blood vessel according to an embodiment of the present invention. FIG. 15 is a perspective view illustrating an anastomosis method using the anastomotic rings 40 and 40' according to an embodiment of the present invention. Referring to FIG. 14, the anastomotic ring 40 is installed on the end of a cut blood vessel, and the blood vessel is fitted on fixing pins 44 provided to the anastomotic ring 40 to prevent the removal of the blood vessel from the anastomotic ring 40 and facilitate the coupling of intimae.

Referring to FIG. 15, the fixing pins 44 installed on the anastomotic ring 40 are coupled to coupling recesses formed in the anastomotic ring 40', and fixing pins 44' installed on the anastomotic ring 40' are coupled to coupling recesses formed in the anastomotic ring 40, thereby improving the coupling of the anastomotic rings 40 and 40'. The anastomotic rings 40 and 40' are installed on two blood vessels, respectively, and the anastomotic rings 40 and 40' are coupled to each other, thereby connecting the blood vessels to each other.

Preferred embodiments of the present invention will be described below in more detail with reference to FIGS. 16 through 27. The present invention may, however, be embodied in different forms and should not be constructed as limited to the embodiments set forth herein. Rather, these embodiments are provided so that this disclosure will be thorough and complete, and will fully convey the scope of the present invention to those skilled in the art. In the drawings, the dimensions of elements may be exaggerated for clarity of illustration.

Figure 16:
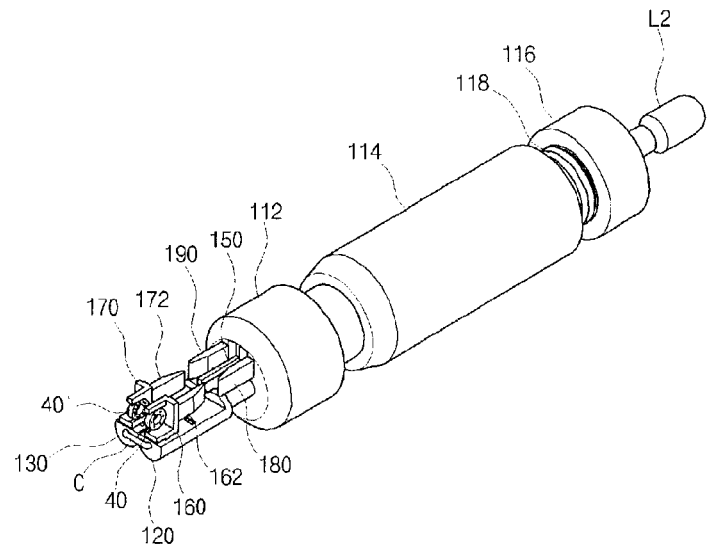
FIG. 16 is a perspective view illustrating an anastomotic device according to an embodiment of the present invention.
Figure 17:
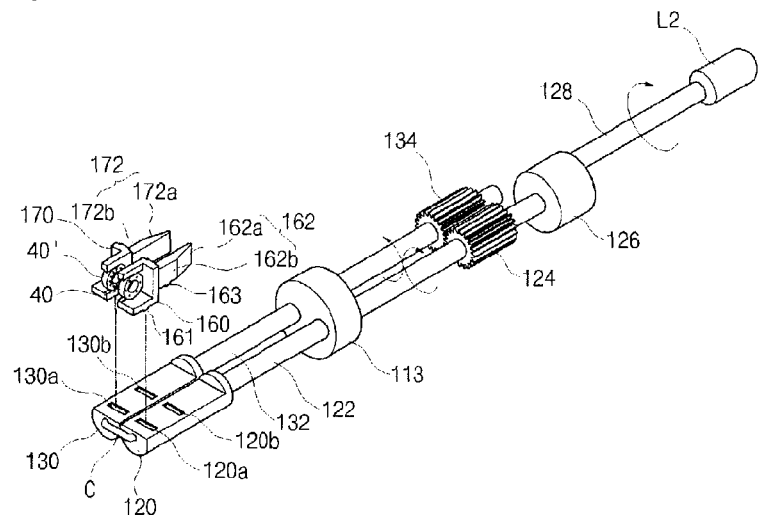
FIG. 17 is a perspective view illustrating the anastomotic device of FIG. 16, without a front case, a middle case, and a rear case.

FIG. 16 is a perspective view illustrating an anastomotic device according to an embodiment of the present invention. FIG. 17 is a perspective view illustrating the anastomotic device of FIG. 16, without a front case, a middle case, and a rear case. Referring to FIGS. 16 and 17, the anastomotic device includes a first holder 160 and a second holder 170. The first and second holders 160 and 170 have an approximately U shape, and are connected to a first rotator 120 and a second rotator 130, respectively, to fix the anastomotic rings 40 and 40' during a medical treatment. After the medical treatment, the anastomotic rings 40 and 40' are removed from the first and second holders 160 and 170. A first slave body 162 and a second slave body 172 are disposed at the rear ends of the first and second holders 160 and 170, respectively. The first and second slave bodies 162 and 172 move according to movements of a first driving body 180 and a second driving body 190, and a moving direction of the first and second driving bodies 180 and 190 is approximately perpendicular to that of the first and second slave bodies 162 and 172, which will be described later.

Referring to FIG. 17, the first slave body 162 has a first slave surface contacting the first driving body 180 to be described later. The first slave surface includes a first slave inclination surface 162a and a first slave plane 162b. The first slave inclination surface 162a is inclined outward to the front side of the first driving body 180, and the first slave plane 162b extends approximately in the moving direction of the first driving body 180 from the front end of the first slave inclination surface 162a. In a same manner, the second slave body 172 has a second slave surface contacting the second driving body 190 to be described later. The second slave surface includes a second slave inclination surface 172a and a second slave plane 172b. The second slave inclination surface 172a is inclined outward to the front side of the second driving body 190, and the second slave plane 172b extends approximately in the moving direction of the second driving body 190 from the front end of the second slave inclination surface 172a. The first and second slave surfaces will be described later in detail.

As illustrated in FIG. 17, the first and second rotators 120 and 130 are disposed at the front end of a first driving shaft 122 and the front end of a slave shaft 132, respectively. The first driving shaft 122 and the first rotator 120 rotate together. The slave shaft 132 and the second rotator 130 rotate together. The clip C includes pins that are inserted in rotation centers of the first and second rotators 120 and 130, respectively. The pins prevent the movement of the first and second rotators 120 and 130 while the first and second rotators 120 and 130 rotate. The first and second rotators 120 and 130 rotate about the pins inserted in the rotation centers thereof.

The first and second rotators 120 and 130 include first guide recesses and second guide recesses. The first and second guide recesses extend approximately in the moving direction of the first and second slave bodies 162 and 172. The first guide recesses include a first front guide recess 120a and a first rear guide recess 120b. The second guide recesses include a second front guide recess 130a and a second rear guide recess 130b. The first holder 160 includes a first front protrusion 161 that is inserted in the first front guide recess 120a. The first slave body 162 includes a first rear protrusion 163 that is inserted in the first rear guide recess 120b. The first front protrusion 161 and the first rear protrusion 163 move along the first front guide recess 120a and the first rear guide recess 120b, respectively. According to a movement of the first slave body 162, the first front protrusion 161 and the first rear protrusion 163 move together with the first holder 160 and the first slave body 162 along the first front guide recess 120a and the first rear guide recess 120b. In a same manner, the second holder 170 and the second slave body 172 include a second front protrusion (not shown) and a second rear protrusion (not shown), respectively. The second front protrusion and the second rear protrusion move along the second front guide recess 130a and the second rear guide recess 130b, respectively. That is, according to a movement of the second slave body 172, the second front protrusion and the second rear protrusion move together with the second holder 170 and the second slave body 172 along the second front guide recess 130a and the second rear guide recess 130b. Accordingly, the anastomotic rings 40 and 40' fixed to the first and second holders 160 and 170 are coupled to each other, which will be described later.

The first driving shaft 122 and the slave shaft 132 pass through a fixing member 113. A first driving gear 124 is installed on the first driving shaft 122. A second driven gear 134 is installed on the slave shaft 132. The first driving gear 124 rotates together with the first driving shaft 122, and the second driven gear 134 rotates together with the slave shaft 132. The second driven gear 134 engages with the first driving gear 124 and rotates according to a rotation of the first driving gear 124.

A first driven gear 126 is installed at the rear end of the first driving shaft 122, and rotates together with the first driving shaft 122. The first driven gear 126 is a ring gear (or an internal gear). A second driving gear 129, which functions as a pinion, is disposed inside the first driven gear 126. The first driven gear 126 rotates according to a rotation of the second driving gear 129, and the first driving shaft 122 rotates according to the rotation of the first driven gear 126. Accordingly, the first driving gear 124 rotates.

Figure 18:
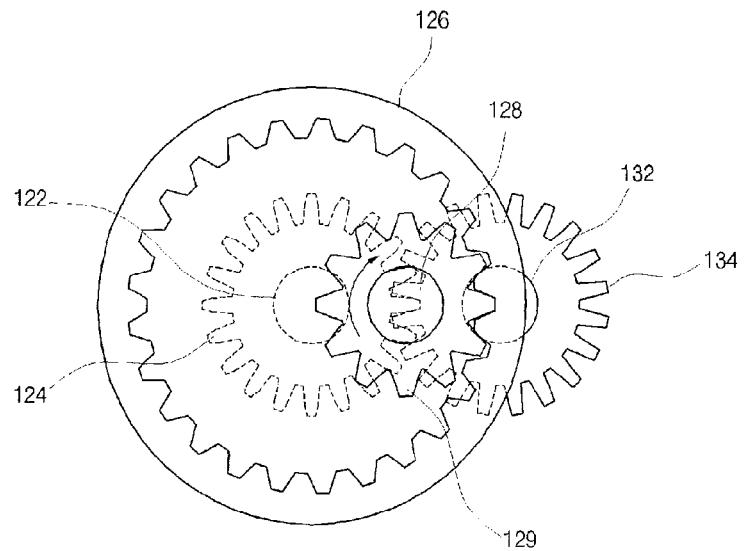
FIG. 18 is a schematic view illustrating connections of first and second driving gears and first and second driven gears as illustrated in FIG. 16.

The second driving gear 129 is fixed to the front end of a second driving shaft 128, and rotates together with the second driving shaft 128. FIG. 18 is a schematic view illustrating connections of the first and second driving gears 124 and 129 and the first and second driven gears 126 and 134 as illustrated in FIG. 17. Referring to FIG. 18, the second driving shaft 128 is disposed between the first driving shaft 122 and the slave shaft 132. Referring to FIG. 16, the second driving shaft 128 is rotatably installed on a rear case 116. The second driving shaft 128 is disposed at the central part of the rear case 116, and a driving lever L2 is disposed at the rear end of the second driving shaft 128. The first driving shaft 122 and the slave shaft 132 will be described later in detail.

Referring to FIG. 16, the anastomotic device includes a front case 112, a middle case 114, the rear case 116, and a screw shaft 118. The first and second driving bodies 180 and 190 and a separation bar 150 are fixed to the front end of the front case 112, and the middle case 114 is disposed between the front case 112 and the rear case 116. The first driving shaft 122 and the slave shaft 132 are exposed out of the front case 112 through the front end of the front case 112. The first and second holders 160 and 170, and the first and second rotators 120 and 130 are disposed at the front side of the front case 112. The driving lever L2 is exposed out of the rear case 116 through the rear end of the rear case 116. The front case 112, the middle case 114, the rear case 116, and the screw shaft 118 may have an approximately circular or polygonal cylinder shape.

Figure 19:
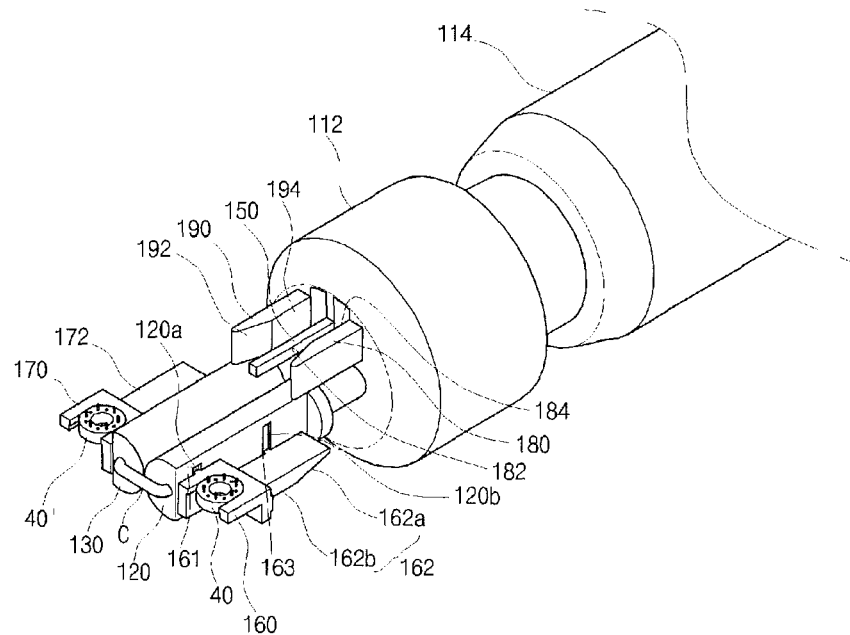
FIGS. 19 through 22 are schematic views illustrating rotations of first and second holders according to rotations of a driving shaft and a slave shaft, illustrated in FIG. 17.
Figure 20:
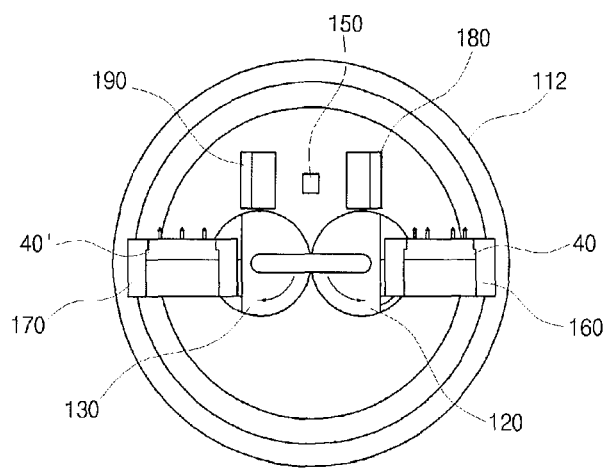

FIGS. 18 through 20 are schematic views illustrating rotations of the first and second holders according to rotations of the first driving shaft and the slave shaft illustrated in FIG. 17. In the state where the second driving gear 129 engages with the first driven gear 126 as illustrated in FIG. 18, when the driving lever L2 connected to the rear end of the second driving shaft 128 is rotated clockwise, the second driving gear 129 rotates to rotate the first driven gear 126 clockwise, and thus, the first driving gear 124 and the first driving shaft 122 rotate clockwise. Thus, the second driven gear 134 rotates counterclockwise, and the slave shaft 132 rotates counterclockwise accordingly.

Figure 21:
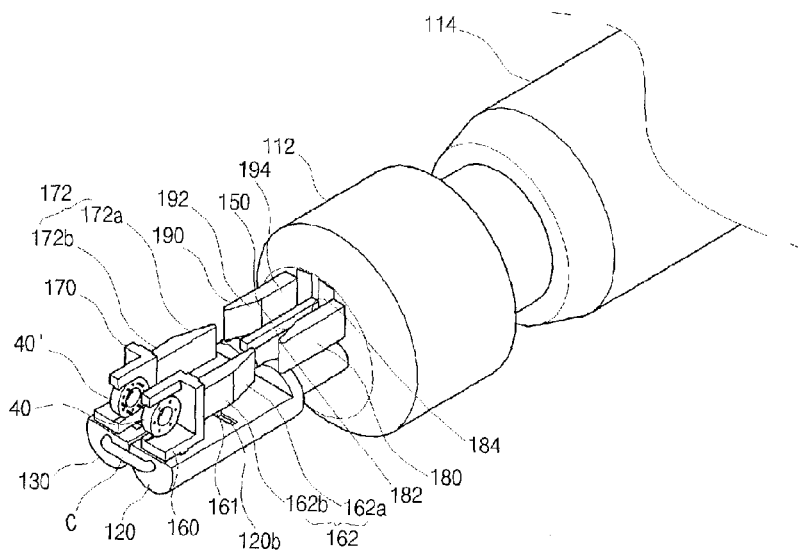
Figure 22:
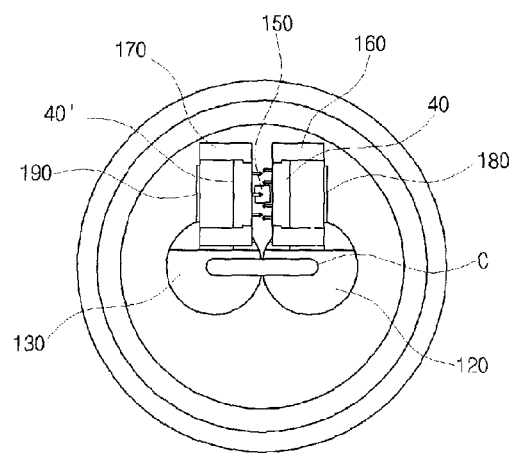

In the state where the anastomotic rings 40 and 40' fixed respectively to the first and second holders 160 and 170 are disposed on approximately the same plane as illustrated in FIGS. 19 and 20, when the driving lever L2 is rotated, the first and second holders 160 and 170 rotate. According to the rotation of the first rotator 120, the anastomotic ring 40 fixed to the first holder 160 is rotated counterclockwise to the second holder 170. According to the rotation of the second rotator 130, the anastomotic ring 40' fixed to the second holder 170 is rotated clockwise to the first holder 160. Referring to FIGS. 21 and 22, according to the rotations of the first and second holders 160 and 170, the anastomotic rings 40 and 40' fixed to the first and second holders 160 and 170 face each other.

At this point, rotational speed of the first driving shaft 122 and rotational speed of the slave shaft 132 are proportional to that of the first driven gear 126. The rotational speed of the first driven gear 126 can be adjusted according to a gear ratio (diameter ratio or ratio in the numbers of teeth) of the first driven gear 126 to the second driving gear 129.

Referring to FIGS. 20 and 22, since the first and second rotators 120 and 130 engage with each other and have the same diameter, when the first and second rotators 120 and 130 rotate, the first and second rotators 120 and 130 are approximately the same in rotational displacement and rotational speed, and thus, can rotate stably.

Figure 23:
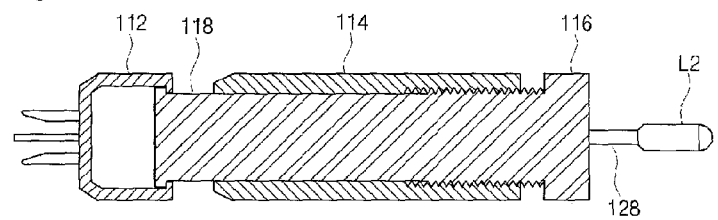
FIGS. 23 and 24 are cross-sectional views illustrating a movement of the front case according to a rotation of the rear case of FIG. 16.
Figure 24:
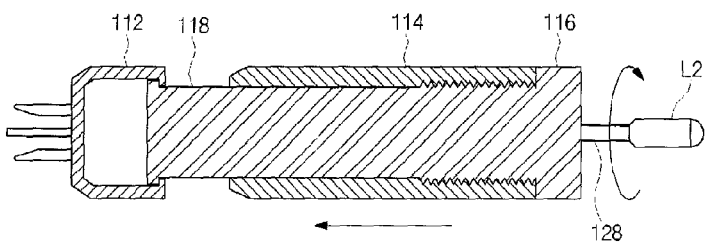
Figure 25:
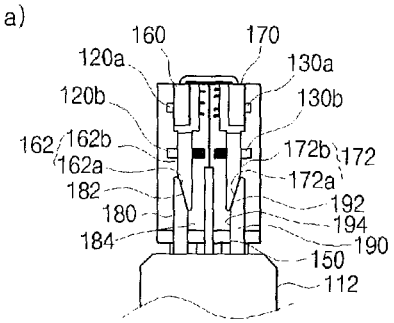
FIGS. 25A, 25B and 25C are schematic views sequentially illustrating movements of first and second slave bodies according to movements of the front case and first and second driving bodies as illustrated in FIG. 16.
Figure 25:
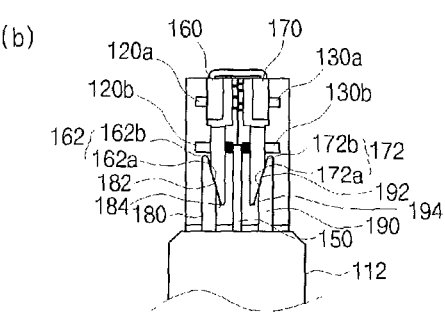
Figure 25:
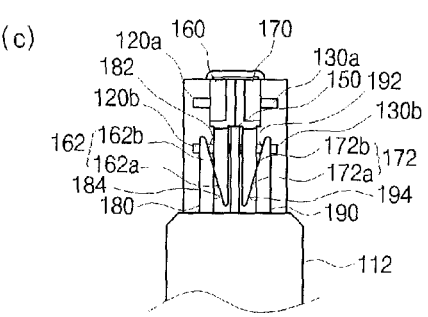

FIGS. 23 and 24 are cross-sectional views illustrating a movement of the front case according to a rotation of the rear case of FIG. 16. Referring to FIG. 23, the front end of the screw shaft 118 is connected to the rear end of the front case 112. The screw shaft 118 freely rotates at the rear end of the front case 112, and torque of the screw shaft 118 is not transmitted to the front case 112. However, when the screw shaft 118 moves forward or rearward, the front case 112 connected to the screw shaft 118 is moved forward or rearward together with the screw shaft 118, which will be described later. The rear end of the screw shaft 118 is connected to the front end of the rear case 116. When the rear case 116 rotates, the screw shaft 118 rotates together with the rear case 116.

The screw shaft 118 passes through the middle case 114. An outer circumferential surface of the screw shaft 118 is provided with a thread. An inner circumferential surface of the middle case 114 is also provided with a thread. The thread of the middle case 114 engages with the thread of the screw shaft 118.

Referring to FIG. 24, when the rear case 116 rotates in a predetermined direction, the thread of the screw shaft 118 moves along the thread of the middle case 114, and the screw shaft 118 moves forward. According to the forward movement of the screw shaft 118, the front case 112 also moves forward. On the contrary, when the screw shaft 118 rotates in the opposite direction to the predetermined direction, the thread of the screw shaft 118 moves along the thread of the middle case 114, and the screw shaft 118 moves rearward. According to the rear movement of the screw shaft 118, the front case 112 also moves rearward.

Figure 26:
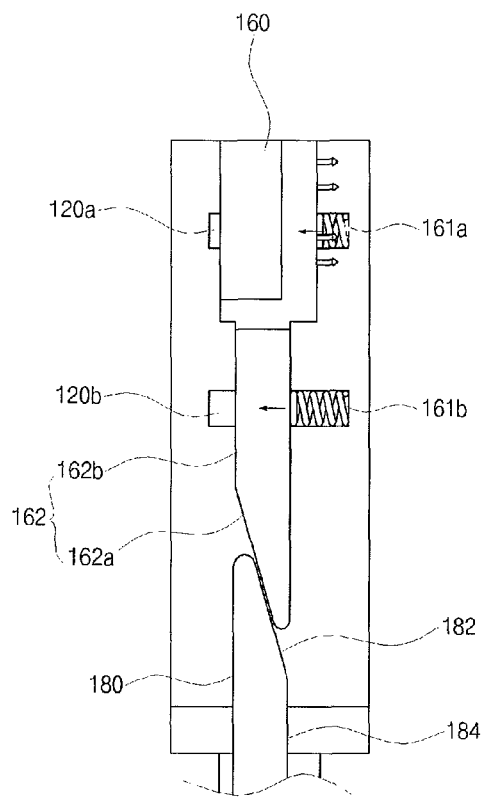
FIG. 26 is a schematic view illustrating a state where the first holder and the first slave body return to their original positions by a first elastic body according to an embodiment of the present invention.

FIGS. 25A, 25B and 25C are schematic views sequentially illustrating movements of the first and second slave bodies according to movements of the front case and the first and second driving bodies as illustrated in FIG. 16. FIG. 26 is a schematic view illustrating a state where the first holder and the first slave body return to their original positions by a first elastic body according to an embodiment of the present invention.

As described above, the separation bar 150 and the first and second driving bodies 180 and 190, fixed to the front end of the front case 112, move together with the front case 112. Referring to FIG. 25A, as the front case 112 moves forward, a first driving inclination surface 182 of the first driving body 180 contacts the first slave inclination surface 162a of the first slave body 162, and a second driving inclination surface 192 of the second driving body 190 contacts the second slave inclination surface 172a of the second slave body 172.

In this state, when the front case 112 moves forward, the first driving inclination surface 182 moves along the first slave inclination surface 162a to apply force to the first slave inclination surface 162a, and thus, the first slave body 162 moves to the second slave body 172. In a same manner, the second driving inclination surface 192 moves along the second slave inclination surface 172a to apply force to the second slave inclination surface 172a, and thus, the second slave body 172 moves to the first slave body 162. Accordingly, as illustrated in FIGS. 25B and 25C, the first and second slave bodies 162 and 172 come close to each other, and the first and second holders 160 and 170 also come close to each other, together with the first and second slave bodies 162 and 172. The moving direction of the first and second slave bodies 162 and 172 is approximately perpendicular to the forward moving direction of the front case 112.

The first protrusion 161 of the first holder 160 and the first rear protrusion 163 of the first slave body 162 move along the first front guide recess 120a and the first rear guide recess 120b. Accordingly, the anastomotic rings 40 and 40' come close to each other and are coupled to each other. Referring to FIG. 26, a first front elastic body 161a and a first rear elastic body 161b are disposed within the first front guide recess 120a and the first rear guide recess 120b, and apply elastic force to the first front protrusion 161 and the first rear protrusion 163. Thus, when the first driving body 180 is moved rearward according to the rear movement of the front case 112, the first holder 160 and the first slave body 162 return to the original positions thereof by the elastic force. This mechanism can be applied to the second holder 170 and the second slave body 172 in a same manner.

Figure 27:
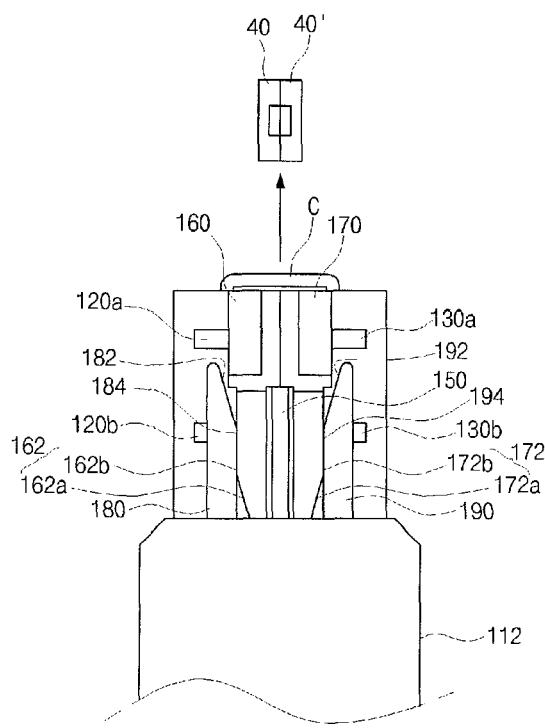
FIG. 27 is a schematic view illustrating a state where anastomotic rings are separated according to movements of the front case and a separation bar of FIG. 16.

FIG. 27 is a schematic view illustrating a state where the anastomotic rings are separated according to movements of the front case and the separation bar of FIG. 16. When the anastomotic rings 40 and 40' fixed to the first and second holders 160 and 170 are coupled to each other, the first and second driving inclination surfaces 182 and 192 are removed from the first and second slave inclination surfaces 162a and 172a, and the first and second driving inclination surfaces 182 and 192 do not apply force to the first and second slave inclination surfaces 162a and 172a any more. After that, as illustrated in FIG. 25C, as the front case 112 moves forward, a first driving plane 184 and a second driving plane 194 move along the first and second slave planes 162b and 172b.

After that, as illustrated in FIG. 27, the separation bar 150 moves forward together with the front case 112, and the separation bar 150 pass through a space disposed between the first and second holders 160 and 170 to push out the anastomotic rings 40 and 40' from the first and second holders 160 and 170. Thus, the anastomotic rings 40 and 40' are removed from the first and second holders 160 and 170.

The above-disclosed subject matter is to be considered illustrative, and not restrictive, and the appended claims are intended to cover all such modifications, enhancements, and other embodiments, which fall within the true spirit and scope of the present invention. Thus, to the maximum extent allowed by law, the scope of the present invention is to be determined by the broadest permissible interpretation of the following claims and their equivalents, and shall not be restricted or limited by the foregoing detailed description.

INDUSTRIAL APPLICABILITY

The present invention may be applied to various types of minute surgeries such as a reconstruction using a free flap method, an anastomosis of a cut blood vessel, an intestinal anastomosis, a treatment of a heart disease, and other anastomoses of tubular organs.

The invention claimed is:
1. An anastomotic device comprising:
a first holder and a second holder for holding a first anastomotic ring and a second anastomotic ring, respectively;
a first slave body connected to the first holder and having a first slave surface;
a second slave body connected to the second holder and having a second slave surface;
a first driving body having a first driving surface sliding along the first slave surface, the first driving body moving along a predetermined direction;
a second driving body having a second driving surface sliding along the second slave surface, the second driving body moving along the predetermined direction,
the first slave body moving toward the second slave body and the second slave body moving toward the first slave body by the movements of the first driving body and the second driving body;
a first rotator connected to the first holder;
a second rotator connected to the second holder;

a driving shaft including a driving gear and having a front end to which the first rotator is fixed; and a slave shaft engaging with the driving gear to rotate and having a front end to which the second rotator is fixed;

wherein the first holder rotates toward the second holder and the second holder rotates toward the first holder by a rotation of the driving shaft.

2. The anastomotic device of claim 1, wherein the first slave surface comprises a first slave inclination surface that is inclined outward to a front side of the first driving body, and a first slave plane that extends approximately in the predetermined direction from a front end of the first slave inclination surface, and the first driving surface comprises a first driving inclination surface that is inclined outward to the front side of the first driving body, and a first driving plane that extends approximately in the predetermined direction from a rear end of the first driving inclination surface, wherein, when the first driving inclination surface slides along the first slave inclination surface, the first salve body moves toward the second slave body.

3. The anastomotic device of claim 2, wherein, when the first driving plane slides along the first slave plane, the first slave body is in a stop state.

4. The anastomotic device of claim 3, further comprising:
a separation bar moving toward the first and second holders along the predetermined direction in the stop state to separate the first and second anastomotic rings from the first and second holders; and
a front case having a front end to which the separation bar and the first and second driving bodies are fixed,
wherein, when the front case moves along the predetermined direction, the separation bar and the first and second driving bodies move along the predetermined direction.

5. The anastomotic device of claim 1, further comprising:
a separation bar moving toward the first and second holders along the predetermined direction to separate the first and second anastomotic rings from the first and second holders; and
a front case having a front end to which the separation bar and the first and second driving bodies are fixed,
wherein, when the front case moves along the predetermined direction, the separation bar and the first and second driving bodies move along the predetermined direction.

6. The anastomotic device of claim 5, further comprising:
a middle case having a first thread on an inner circumferential surface thereof; and
a screw shaft having a second thread on an outer circumferential surface thereof to correspond to the first thread and having a front end connected to the front case to move along the predetermined direction by a rotation of the screw shaft.

7. The anastomotic device of claim 5, further comprising:
a rear case disposed behind the front case;
a pinion disposed inside the rear case;
a rotation lever connected to the pinion to rotate the pinion; and
a rack member having a front end holding the front case to move together with the front case and including a rack engaging with the pinion and moving along the predetermined direction by a rotation of the pinion.

8. The anastomotic device of claim 1, wherein the first rotator includes a first guide recess extending in a direction approximately perpendicular to the predetermined direction, and wherein the first holder includes a first protrusion that is inserted in the first guide recess and moves along the first guide recess.

9. The anastomotic device of claim 1, wherein the first rotator includes a first front guide recess and a first rear guide recess, the first front guide recess is connected to the first holder and extends in a direction approximately perpendicular to the predetermined direction, the first rear guide recess is connected to the first slave body and extends in the direction approximately perpendicular to the predetermined direction, the first holder includes a first front protrusion that is inserted in the first front guide recess to move along the first front guide recess, and the first slave body includes a first rear protrusion that is inserted in the first rear guide recess to move along the first rear guide recess.

10. The anastomotic device of claim 9, further comprising:
a first front elastic body inserted in the first front guide recess to apply elastic force to the first holder such that first holder returns from the second holder; and
a first rear elastic body inserted in the first rear guide recess to apply elastic force to the first slave body such that first slave body returns from the second slave body.

11. An anastomotic device comprising:
a first holder and a second holder for holding a first anastomotic ring and a second anastomotic ring, respectively;
a first slave body connected to the first holder and having a first slave surface;
a second slave body connected to the second holder and having a second slave surface;
a first driving body having a first driving surface sliding along the first slave surface, the first driving body moving along a predetermined direction;
a second driving body having a second driving surface sliding along the second slave surface, the second driving body moving along the predetermined direction,
the first slave body moving toward the second slave body and the second slave body moving toward the first slave body by the movements of the first driving body and the second driving body;
a first rotator connected to the first holder;
a first driving shaft including a first driving gear and a first driven gear and having a front end to which the first rotator is fixed;
a second rotator connected to the second holder;
a slave shaft including a second driven gear engaging with the first driving gear to rotate and having a front end to which the second rotator is fixed; and
a second driving shaft including a second driving gear engaging with the first driven gear to rotate,
wherein the first holder rotates toward the second holder and the second holder rotates toward the first holder by the rotation of the second driving shaft.

12. The anastomotic device of claim 11, wherein the first driven gear comprises a ring gear, and the second driving gear comprises a pinion engaging with an inner part of the ring gear.

13. The anastomotic device of claim 11, wherein the second driving shaft is disposed between the first driving shaft and the slave shaft.

14. The anastomotic device of claim 11, wherein the first slave surface comprises a first slave inclination surface that is inclined outward to a front side of the first driving body and a first slave plane that extends approximately in the predetermined direction from a front end of the first slave inclination surface,
  wherein the first driving surface comprises a first driving inclination surface that is inclined outward to the front side of the first driving body, and a first driving plane that extends approximately in the predetermined direction from a rear end of the first driving inclination surface, and
  wherein, when the first driving inclination surface slides along the first slave inclination surface, the first salve body moves toward the second slave body.

15. The anastomotic device of claim 14, wherein, when the first driving plane slides along the first slave plane, the first slave body is in a stop state.

* * * * *